United States Patent
Ogawa

(10) Patent No.: US 6,339,636 B1
(45) Date of Patent: Jan. 15, 2002

(54) RADIATION IMAGE RECORDING METHOD AND APPARATUS

(75) Inventor: Eiji Ogawa, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/531,748

(22) Filed: Mar. 20, 2000

(30) Foreign Application Priority Data

Mar. 19, 1999 (JP) ............................................. 11-076037

(51) Int. Cl.$^7$ ............................................. G01N 23/04
(52) U.S. Cl. ....................................... 378/146; 378/149
(58) Field of Search ................................. 378/145, 146, 378/147, 148, 149, 4, 901, 150, 151, 152, 153, 155

(56) References Cited

U.S. PATENT DOCUMENTS

| | | | | |
|---|---|---|---|---|
| 4,096,391 A | * | 6/1978 | Barnes ........................ | 378/146 |
| 4,675,893 A | * | 6/1987 | Duinker et al. ............. | 378/145 |
| 5,054,048 A | * | 10/1991 | Wang ........................... | 378/146 |
| 5,136,627 A | * | 8/1992 | Conrads et al. ............. | 378/146 |
| 5,164,976 A | * | 11/1992 | Scheid et al. ............... | 378/146 |
| 5,233,193 A | * | 8/1993 | Arakawa ...................... | 378/146 |
| 5,305,367 A | * | 4/1994 | Mulder ........................ | 378/146 |
| 5,812,629 A | * | 9/1998 | Clauser ......................... | 378/7 |
| 5,848,114 A | | 12/1998 | Kawai et al. .................. | 378/4 |

* cited by examiner

*Primary Examiner*—Robert H. Kim
*Assistant Examiner*—Drew A. Dunn
(74) *Attorney, Agent, or Firm*—Sughrue Mion, PLLC

(57) ABSTRACT

A radiation source and a radiation detector are located with an object intervening therebetween. A set of radiation blocking plates, each of which has at least one slit, are located between the radiation source and the radiation detector such that the object intervenes between the radiation blocking plates, and such that the slits of the radiation blocking plates are aligned in a straight line with the radiation source. The set of the radiation blocking plates are shifted stepwise in a direction along which radiation having been produced by the radiation source scans the object, such that the state in which the slits of the radiation blocking plates and the radiation source are aligned with one another in the straight line is kept. After each step of the shifting, the radiation source, the set of the radiation blocking plates, and the radiation detector are rotated around the object. Radiation image patterns of the object are recorded during the rotation.

4 Claims, 4 Drawing Sheets

F I G. 3A
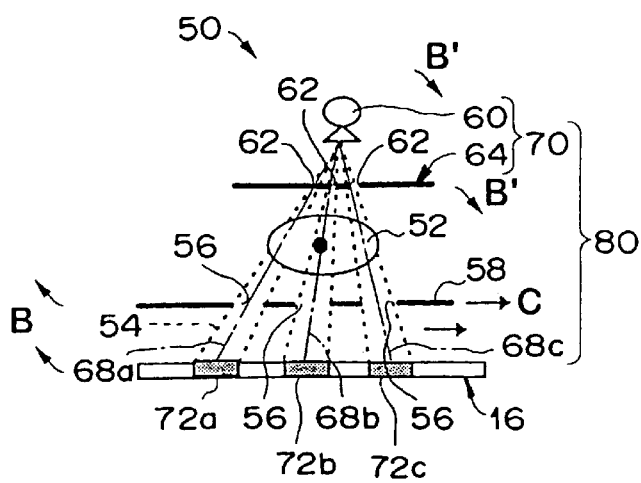
F I G. 3B
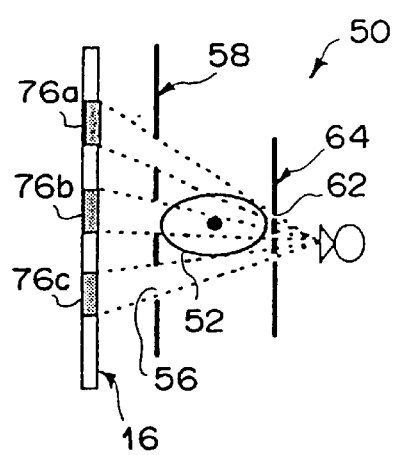
F I G. 3C
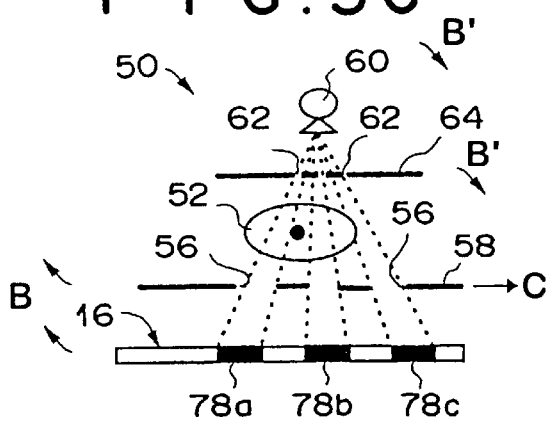
F I G. 3D
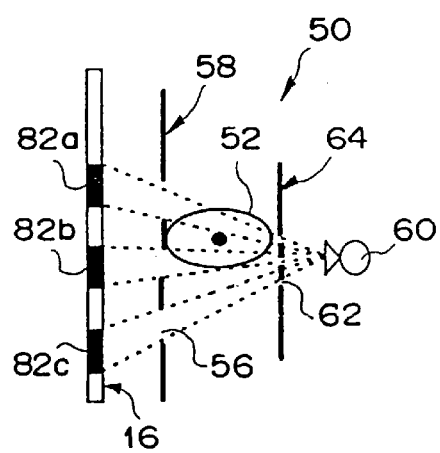
F I G. 4A
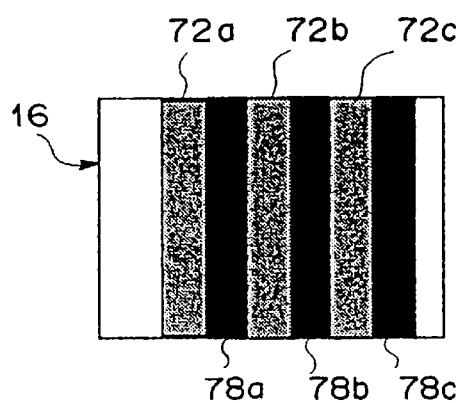
F I G. 4B
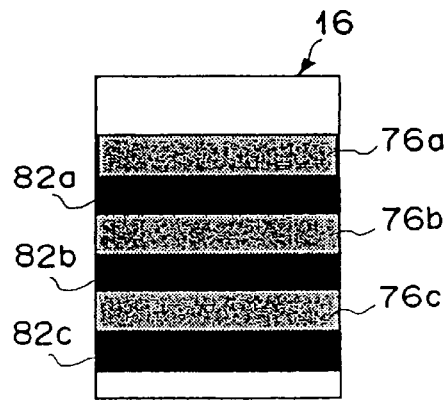

RADIATION IMAGE RECORDING METHOD AND APPARATUS

BACKGROUND OF THE INVENTION

1. Field of the Invention

This invention relates to a radiation image recording method and apparatus. This invention particularly relates to a radiation image recording method and apparatus for use in a cone-beam computed tomography system (a cone-beam CT system).

2. Description of the Prior Art

Techniques for recording and reproducing radiation images have widely been used in practice, wherein a radiation image having been obtained by irradiating radiation to an object and causing the radiation carrying image information of the object to impinge upon a radiation detector is converted into an image signal, the image signal is subjected to appropriate image processing, and a visible image is reproduced from the processed image signal. FIG. 6 is a perspective view showing a conventional X-ray tomographic image recording apparatus 100, in which X-rays 108 are irradiated in a cone beam-like form to an object 102. The X-ray tomographic image recording apparatus 100 is disclosed in, for example, Japanese Unexamined Patent Publication No. 9(1997)-253079. The X-ray tomographic image recording apparatus 100 comprises an X-ray source 104 and a two-dimensional detector 106, which are located so as to stand facing each other with the object 102 intervening therebetween. The X-ray source 104 and the two-dimensional detector 106 are rotated in a pair around the object 102. During the rotation, at a plurality of positions of rotation, the X-rays 108 carrying image information of the object 102 are detected as X-ray images by the two-dimensional detector 106. X-ray image signals representing the X-ray images having thus been obtained are fed into an image processing section 110 and utilized for reconstructing a three-dimensional image. In this manner, a tomographic image of a desired cross-section of the object can be obtained.

However, with the cone beam-like X-rays 108, the range irradiated simultaneously to the X-rays 108 is wide. Therefore, when the cone beam-like X-rays 108 passes through the object 102, much scattered X-rays occur. The problems thus occur in that the scattered X-rays impinge upon the two-dimensional detector 106, and much noise occurs in the detected image. In order to solve the problems with regard to noise due to the scattered X-rays, a technique has heretofore been utilized, wherein a scattered radiation removing grid is located between the object 102 and the two-dimensional detector 106 in order to remove the scattered X-rays occurring when the X-rays 108 pass through the object 102.

However, in cases where the scattered radiation removing grid is located between the object 102 and the two-dimensional detector 106, even if the scattered X-rays are removed by the grid, the problems occur in that the grid causes moire to occur in the image during the image processing. Further, part of the X-rays 108 carrying the image information of the object 102 is absorbed by the grid, and a signal-to-noise ratio of the detected image signal becomes low.

SUMMARY OF THE INVENTION

The primary object of the present invention is to provide a radiation image recording method, wherein scattered radiation is capable of being removed efficiently such that no loss of an image signal due to a grid occurs.

Another object of the present invention is to provide an apparatus for carrying out the radiation image recording method.

The present invention provides a radiation image recording method, comprising the steps of:

i) locating a radiation source and a radiation detector with an object intervening therebetween, ii) locating a set of radiation blocking plates, each of which has at least one slit, between the radiation source and the radiation detector such that the object intervenes between the radiation blocking plates, and such that the slits of the radiation blocking plates are aligned in a straight line with the radiation source, iii) shifting the set of the radiation blocking plates stepwise in a direction along which radiation having been produced by the radiation source scans the object, such that the state in which the slits of the radiation blocking plates and the radiation source are aligned with one another in the straight line is kept, iv) after each step of the shifting, rotating the radiation source, the set of the radiation blocking plates, and the radiation detector around the object, and v) recording radiation image patterns of the object during the rotation.

The term "radiation scanning an object" as used herein means that the radiation, which has passed through the slit of the radiation blocking plate close to the radiation source and has been shaped by the slit into a fan beam, moves with respect to the object and in the direction which intersects with the plane of the fan beam.

The present invention also provides a radiation image recording apparatus, comprising:

i) a radiation source, ii) a radiation detector, which is located so as to stand facing the radiation source with an object intervening between the radiation detector and the radiation source, iii) a set of radiation blocking plates, each of which has at least one slit and which are located between the radiation source and the radiation detector such that the object intervenes between the radiation blocking plates, and such that the slits of the radiation blocking plates are aligned in a straight line with the radiation source, iv) means for shifting the set of the radiation blocking plates stepwise in a direction along which radiation having been produced by the radiation source and having been shaped by the slit of the radiation blocking plate close to the radiation source into a fan beam scans the object, such that the state in which the slits of the radiation blocking plates and the radiation source are aligned with one another in the straight line is kept, v) means for rotating the radiation source, the set of the radiation blocking plates, and the radiation detector around the object after each step of the shifting, and vi) image recording means for recording radiation image patterns of the object at a plurality of positions of rotation during the rotation.

With the radiation image recording method and apparatus in accordance with the present invention, the set of the radiation blocking plates, each of which has at least one slit, are located with the object intervening therebetween. The set of the radiation blocking plates are shifted stepwise in the direction along which the radiation having been produced by the radiation source scans the object, such that the state in which the slits of the radiation blocking plates and the radiation source are aligned with one another in the straight line is kept. Also, after each step of the shifting, the radiation source, the set of the radiation blocking plates, and the radiation detector are rotated around the object. During the rotation, radiation image patterns of the object are recorded. Therefore, the radiation image recording method and apparatus in accordance with the present invention have the effects described below. Specifically, the radiation having been produced by the radiation source is restricted by the slit of the radiation blocking plate, which is close to the radiation source, into a fan beam-like shape. The fan beam impinges upon the object. Therefore, little scattered radiation occurs when the fan beam passes through the object. Also, the scattered radiation coming from the object is removed by the slit of the radiation blocking plate, which is close to the radiation detector. As a result, image patterns containing little noise can be obtained. Further, the set of the radiation blocking plates are shifted stepwise, the entire image recording system is rotated around the object after each step of the shifting, and the radiation image patterns of the object are recorded during the rotation. In this manner, the image patterns of the entire area of the object are obtained. From the thus obtained image patterns, a three-dimensional image having good image quality can be reconstructed. In cases where each of the radiation blocking plates has a plurality of slits, and a plurality of fan beams are formed, a large amount of signal can be obtained from a single recording operation. Therefore, in such cases, the image recording operations can be performed quickly, and the image recording efficiency can be kept high.

BRIEF DESCRIPTION OF THE DRAWINGS

FIG. 3A is a schematic view showing relationship between an object and an image recording section at the time of a rotation angle of the image recording section of zero degree in a second embodiment of the radiation image recording apparatus in accordance with the present invention, FIG. 3B is a schematic view showing relationship between the object and the image recording section at the time of a rotation angle of the image recording section of 90 degrees in the second embodiment, FIG. 3C is a schematic view showing relationship between the object and the image recording section at the time of a rotation angle of the image recording section of zero degree after the shifting of radiation blocking plates in the second embodiment, FIG. 3D is a schematic view showing relationship between the object and the image recording section at the time of a rotation angle of the image recording section of 90 degrees after the shifting of the radiation blocking plates in the second embodiment, FIG. 4A is a plan view showing radiation image patterns recorded at the time of a rotation angle of the image recording section of zero degree in the second embodiment, FIG. 4B is a plan view showing radiation image patterns recorded at the time of a rotation angle of the image recording section of 90 degrees in the second embodiment.

DESCRIPTION OF THE PREFERRED EMBODIMENTS

The present invention will hereinbelow be described in further detail with reference to the accompanying drawings.

Figure 1A:
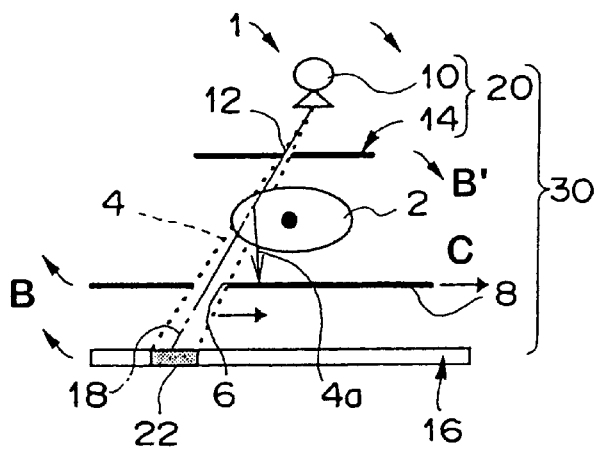
FIG. 1A is a schematic view showing relationship between an object and an image recording section at the time of a rotation angle of the image recording section of zero degree in a first embodiment of the radiation image recording apparatus in accordance with the present invention.
Figure 1B:
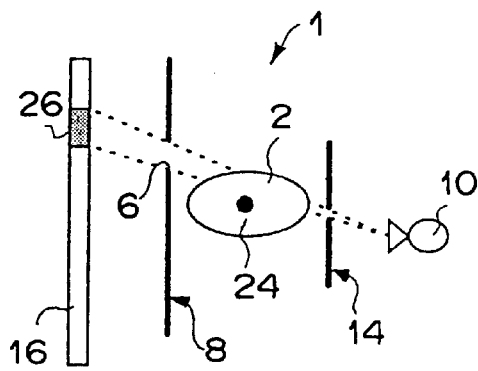
FIG. 1B is a schematic view showing relationship between the object and the image recording section at the time of a rotation angle of the image recording section of 90 degrees in the first embodiment.
Figure 1C:
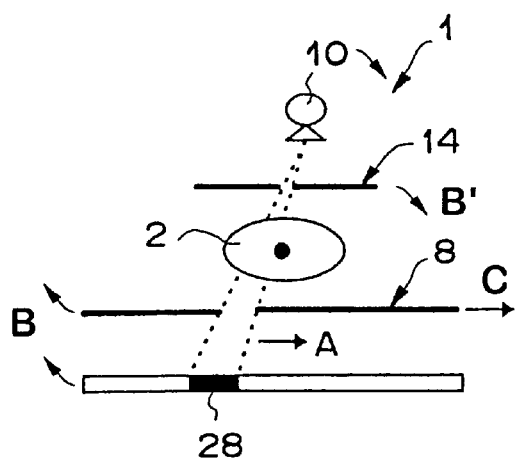
FIG. 1C is a schematic view showing relationship between the object and the image recording section at the time of a rotation angle of the image recording section of zero degree after the shifting of radiation blocking plates in the first embodiment.
Figure 1D:
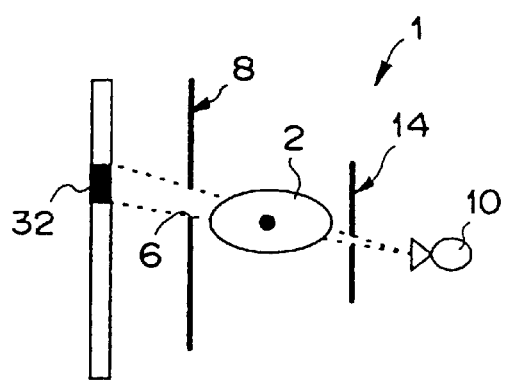
FIG. 1D is a schematic view showing relationship between the object and the image recording section at the time of a rotation angle of the image recording section of 90 degrees after the shifting of the radiation blocking plates in the first embodiment.
Figure 2A:
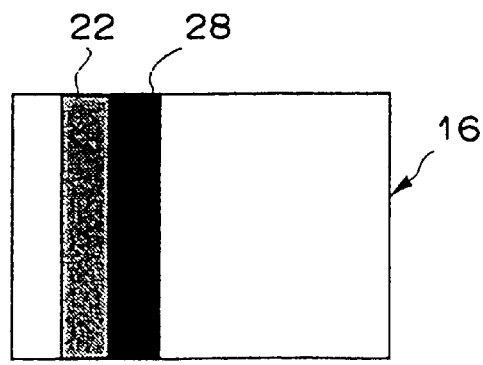
FIG. 2A is a plan view showing radiation image patterns recorded at the time of a rotation angle of the image recording section of zero degree in the first embodiment.
Figure 2B:
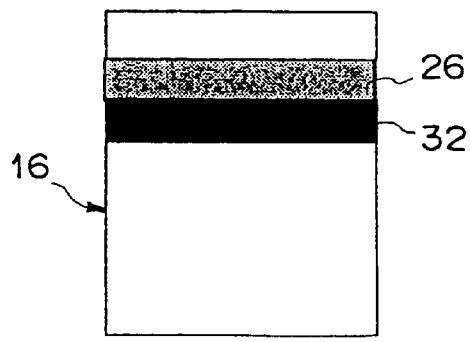
FIG. 2B is a plan view showing radiation image patterns recorded at the time of a rotation angle of the image recording section of 90 degrees in the first embodiment.

FIGS. 1A, 1B, 1C, and 1D are schematic views showing a radiation image recording apparatus 1, which is a first embodiment of the radiation image recording apparatus in accordance with the present invention. FIG. 1A shows a relationship between an object 2 and an image recording section 30 at the time of a rotation angle of the image recording section 30 of zero degrees, wherein an image pattern of the object 2 is recorded with X-rays (radiation) 4 having been set in a predetermined direction. FIG. 1B shows the relationship between the object 2 and the image recording section 30, wherein the direction of the X-rays 4 with respect to the object 2 has been rotated 90 degrees from that in FIG. 1A. The change in position of the image recording section 30 relative to the object 2 is provided by rotation of the apparatus components in the directions B and B'. FIG. 1C shows the relationship between the object 2 and the image recording section 30 at the time of a rotation angle of the image recording section 30 of zero degree after the direction of irradiation of the X-rays 4 has been shifted one step toward the center point of the object 2. The step-wise change in direction A can be achieved by a step-wise shift of the blocking plates in the direction C. FIG. 1D shows the relationship between the object 2 and the image recording section 30, wherein the direction of the X-rays 4 with respect to the object 2 has been rotated 90 degrees from that in FIG. 1C. FIG. 2A is a plan view showing radiation image patterns recorded at the time of a rotation angle of the image recording section 30 of zero degree in the first embodiment. FIG. 2B is a plan view showing radiation image patterns recorded at the time of a rotation angle of the image recording section 30 of 90 degrees in the first embodiment.

With reference to FIG. 1A, the object 2 is a human body as viewed from the head side or the foot side. A radiation blocking plate (a first radiation blocking plate) 8 having a slit (a first slit) 6 is located below the object 2. A radiation blocking plate (a second radiation blocking plate) 14 having a slit (a second slit) 12 is located above the object 2 and in parallel with the radiation blocking plate 8. It is sufficient for the slit 6 and the slit 12 to be aligned in a straight line with a radiation source 10, and the radiation blocking plate 8 and the radiation blocking plate 14 need not necessarily be parallel with each other. The radiation source 10 is located above the radiation blocking plate 14, and a radiation detector 16 is located below the radiation blocking plate 8. The combination of the radiation source 10 and the radiation blocking plate 14 is herein referred to as a radiation irradiating means 20. The combination of the radiation irradiating means 20, the radiation blocking plates 8 and 14, and the radiation detector 16 is herein referred to as the image recording section 30. As illustrated in FIG. 1C, even after the radiation blocking plates 8 and 14 are shifted stepwise as will be described later, the radiation source 10, the slit 12 of the radiation blocking plate 14, and the slit 6 of the radiation blocking plate 8 are kept in the state of being aligned in a straight line with one another.

The X-rays 4 having been produced by the radiation source 10 have a cone beam-like shape. The X-rays 4 are then restricted by the slit 12 of the radiation blocking plate 14 into a fan beam-like shape, and the X-rays 4 taking on the form of the fan beam are irradiated to the object 2. Therefore, the problems do not occur in that, as in the cases where a cone beam impinges upon the object 2, a wide range of scattered X-rays occur when the X-rays 4 pass through the object 2. The X-rays 4 having been restricted into the fan beam impinge upon the object 2 and pass through it. Of the X-rays 4, primary passing X-rays 18 pass approximately straightly from the radiation source 10 through the object 2. The position of the slit 6 is adjusted so as to align with the primary passing X-rays 18.

When the X-rays 4 having passed through the slit 12 of the radiation blocking plate 14 pass through the object 2, scattered X-rays 4a may occur. The scattered X-rays 4a do not pass through the slit 6 and are blocked by the radiation blocking plate 8. The primary passing X-rays 18 pass through the slit 6, impinge upon the radiation detector 16, and form an X-ray image pattern 22. At this time, the X-ray image pattern 22 is formed by the X-rays 4 having passed through an inner peripheral area of the object 2. In FIG. 1A, the X-ray image pattern 22 is indicated as a shadow on the radiation detector 16. As illustrated in FIG. 2A, the X-ray image pattern 22 is formed in a long narrow pattern at the left area of the radiation detector 16.

As illustrated in FIG. 1A, the slit 12 of the radiation blocking plate 14 is set to be narrower than the slit 6 of the radiation blocking plate 8. In this embodiment, the width of the slit 12 is set at 5 mm, and the width of the slit 6 is set at 15 mm. The ratio of the width of the slit 12 to the width of the slit 6 is in proportion to the ratio of the distance between the radiation source 10 and the radiation blocking plate 14 to the distance between the radiation source 10 and the radiation blocking plate 8. Specifically, in this embodiment, if the distance between the radiation source 10 and the radiation blocking plate 14 is taken as 1, the distance between the radiation source 10 and the radiation blocking plate 8 will be 3. Therefore, the radio of the width of the slit 12 to the width of the slit 6 is set at 1:3. The width of the slit 12 and the width of the slit 6 are set at appropriate values in accordance with the distances from the radiation source 10.

In the state of FIG. 1A in which the object 2, the radiation blocking plates 8 and 14, and the radiation detector 16 are parallel with one another, the rotation angle of the image recording section 30 is taken as zero degree. FIG. 1B shows the state in which the image recording section 30 has been rotated 90 degrees clockwise, and an image pattern of a different site of the object 2 is recorded. In this case, the center of rotation is a point 24 within the object 2. However, the object 2 and the center of rotation 24 need not necessarily coincide with each other. The relationship between the position of the radiation blocking plate 8 and the position of the radiation blocking plate 14 is kept the same as in FIG. 1A. Also, the angle of the primary passing X-rays 18 with respect to the radiation detector 16 is kept at a predetermined angle.

By way of example, FIG. 1B shows the state in which the image recording section 30 has been rotated 90 degrees. While the image recording section 30 is being rotated, image patterns are recorded continuously or at intervals of a small rotation angle. Signal components obtained from the radiation detector 16, which represent the thus recorded image patterns, are stored in an image storing section 88 shown in FIG. 5, which will be described later. As illustrated in FIG. 2B, when the rotation angle of the image recording section 30 is 90 degrees, an X-ray image pattern is formed at an area 26 of the radiation detector 16. In this manner, the image recording section 30 is rotated one turn, a plurality of image patterns of the object 2 are recorded, and one step of the image recording operation is finished.

Thereafter, as illustrated in FIG. 1C, the image recording section 30 is set at the position of the rotation angle of zero degree, and the radiation blocking plate 8 and the radiation blocking plate 14 are shifted one step toward the right as indicated by the arrow A by being synchronized with each other. In this manner, the direction of irradiation of the X-rays 4 is directed to a site of the object 2, which site is adjacent to the site exposed to the X-rays 4 in the state shown in FIG. 1A. At this time, as illustrated in FIG. 2A, an X-ray image pattern 28 adjacent to the X-ray image pattern 22 is recorded. Also, in the same manner as that described above, the image recording section 30 is rotated, and image patterns of the object 2 are recorded. As illustrated in FIG. 1D and FIG. 2B, when the rotation angle of the image recording section 30 is 90 degrees, an X-ray image pattern 32 is formed on the radiation detector 16. In this manner, image patterns of a plurality of sites of the object 2 are recorded. Thereafter, in an image processing section 92 shown in FIG. 5, which will be described later, a single X-ray image is composed from the plurality of the recorded image patterns, and a three-dimensional image is reconstructed.

In the first embodiment described above, the radiation blocking plate 8 has only one slit 6, and the radiation blocking plate 14 has only one slit 12. Alternatively, each radiation blocking plate may have a plurality of slits. A second embodiment of the radiation image recording apparatus in accordance with the present invention, wherein each radiation blocking plate has a plurality of slits, will be described hereinbelow with reference to FIGS. 3A, 3B, 3C, 3D, and FIGS. 4A, 4B. FIGS. 3A, 3B, 3C, and 3D are schematic views showing a radiation image recording apparatus 50, which is the second embodiment of the radiation image recording apparatus in accordance with the present invention. FIG. 3A shows a relationship between an object 52 and an image recording section 80 at the time of a rotation angle of the image recording section 80 of zero degrees, wherein image patterns of the object 52 are recorded with X-rays 54 having been set in predetermined directions. FIG. 3B shows the relationship between the object 52 and the image recording section 80, wherein the directions of the X-rays 54 with respect to the object 52 have been rotated 90 degrees from those in FIG. 3A. The change in position of the image recording section 80 relative to the object 52 is provided by rotation of the apparatus components in the directions B and B'. FIG. 3C shows the relationship between the object 52 and the image recording section 80 at the time of a rotation angle of the image recording section 80 of zero degree after the directions of irradiation of the X-rays 54 have been shifted one step toward the center point of the object 52. This step-wise shift can be achieved by a step-wise shift of the blocking plates in the direction C. FIG. 3D shows the relationship between the object 52 and the image recording section 80, wherein the directions of the X-rays 4 with respect to the object 52 have been rotated 90 degrees from those in FIG. 3C. FIG. 4A is a plan view showing radiation image patterns recorded at the time of a rotation angle of the image recording section 80 of zero degree in the second embodiment. FIG. 4B is a plan view showing radiation image patterns recorded at the time of a rotation angle of the image recording section 80 of 90 degrees in the second embodiment.

With reference to FIG. 3A, a radiation blocking plate (a first radiation blocking plate) 58 has three slits 56, 56, 56, and a radiation blocking plate (a second radiation blocking plate) 64 has three slits 62, 62, 62. As in the first embodiment described above, each slit 56 of the radiation blocking plate 58 and the corresponding slit 62 of the radiation blocking plate 64 are aligned in a straight line with a radiation source 60 which produces the X-rays 54. Also, the slits 62, 62, 62 of the radiation blocking plate 64 restrict the X-rays 54, which have been produced by the radiation source 60, into three fan beams. The combination of the radiation source 60 and the radiation blocking plate 64 is herein referred to as a radiation irradiating means 70. The combination of the radiation irradiating means 70, the radiation blocking plate 58, and the radiation detector 16 is herein referred to as the image recording section 80. When the image recording section 80 is set at the position of the rotation angle of zero degree as shown in FIG. 3A, X-ray image patterns 72a, 72b, and 72c of the object 52 are recorded as shown in FIG. 3A and FIG. 4A. The X-ray image patterns 72a, 72b, and 72c, respectively, are formed by primary passing X-rays 68a, 68b, and 68c, which have passed through the slits 62, 62, 62 and the corresponding slits 56, 56, 56.

When the image recording section 80 has been rotated 90 degrees from the position of FIG. 3A as shown in FIG. 3B, X-ray image patterns 76a, 76b, and 76c are recorded as shown in FIG. 3B and FIG. 4B. At this time, the X-ray image patterns 76a, 76b, and 76c are formed with the X-rays 54 irradiated to the object 52 from its lateral side.

Thereafter, as illustrated in FIG. 3C, the image recording section 80 is set at the position of the rotation angle of zero degree, and the radiation blocking plate 64 and the radiation blocking plate 58 are shifted one step toward the right by being synchronized with each other. In this manner, the directions of irradiation of the X-rays 54 are directed to sites of the object 52, which sites are adjacent to the sites exposed to the X-rays 54 in the state shown in FIG. 3A. At this time, as illustrated in FIG. 4A, X-ray image patterns 78a, 78b, and 78c adjacent to the X-ray image patterns 72a, 72b, and 72c are recorded. Also, in the same manner as that described above, the image recording section 80 is rotated, and image patterns of the object 52 are recorded. As illustrated in FIG. 3D and FIG. 4B, when the rotation angle of the image recording section 80 is 90 degrees, X-ray image patterns 82a, 82b, and 82c are formed on the radiation detector 16. In the second embodiment, wherein each of the radiation blocking plate 58 and the radiation blocking plate 64 has the three slits and the range of irradiation of the X-rays 54 is wide, the X-ray image patterns of the entire area of the object 52 can be obtained with only two times of rotations of the image recording section 80. In cases where the intervals of the slits are small, the scattered X-rays can be removed efficiently, but the number of times of the image recording operations becomes large. In cases where resolution may be sacrificed slightly and the efficiency should be kept high, the intervals of the slits 56, 56, 56 and the intervals of the slits 62, 62, 62 may be set at large values.

Figure 5:
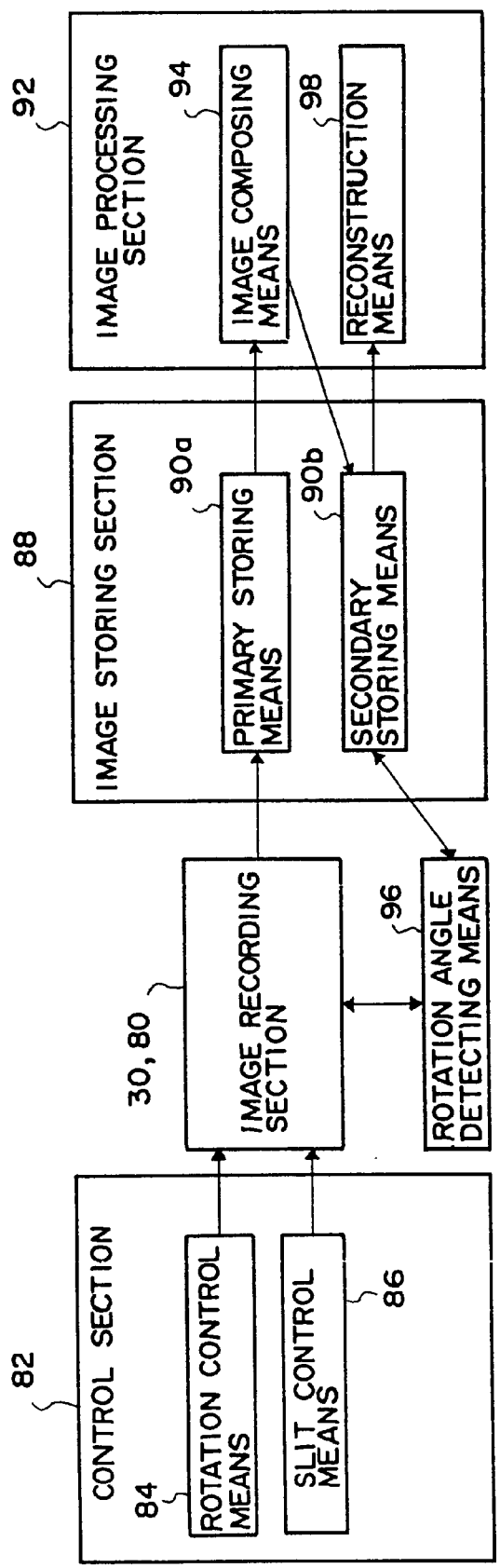
FIG. 5 is a block diagram showing an image forming system, in which the first or second embodiment of the radiation image recording apparatus in accordance with the present invention is employed.
Figure 6:
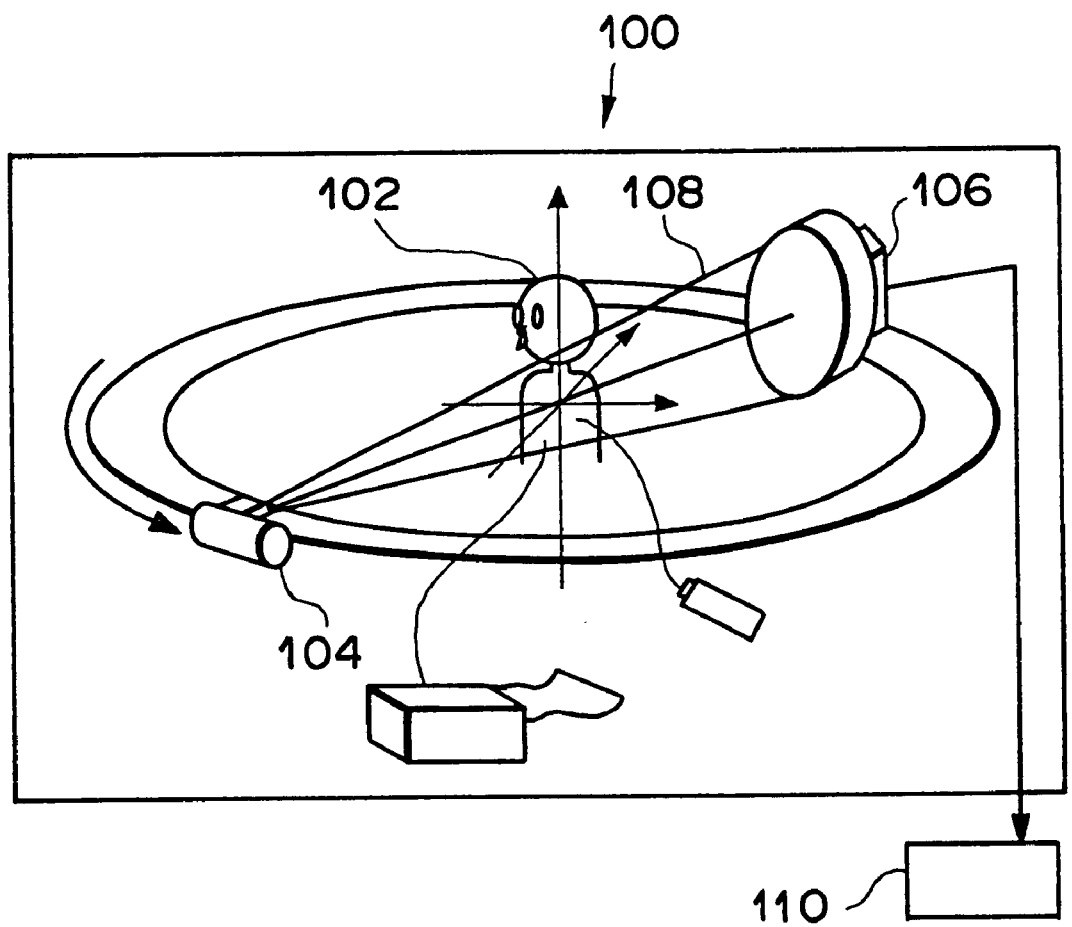
FIG. 6 is a perspective view showing an example of a conventional radiation image recording apparatus.

FIG. 5 is a block diagram showing an image forming system, in which the first or second embodiment of the radiation image recording apparatus in accordance with the present invention is employed. The rotation of the image recording section 30 or the image recording section 80 is controlled by rotation control means 84 of a control section 82. The shifting of the radiation blocking plates 8, 14 or the radiation blocking plates 58, 64 is controlled by slit control means 86 of the control section 82. Signal components representing the X-ray image patterns 22, 26, 28, 32, and the like, which have been recorded at the image recording section 30, or the X-ray image patterns 72, 76, 78, 82, and the like, which have been recorded at the image recording section 80, are stored in primary storing means 90a of the image storing section 88. The primary storing means 90a may utilize an optical disk, a magnetic disk, or the like. The signal components having been stored in the primary storing means 90a are fed into image composing means 94 of the image processing section 92 and utilized for composing a single image. The image signal representing the composed image is stored in secondary storing means 90b of the image storing section 88. The secondary storing means 90b may utilize an optical disk, a magnetic disk, or the like. Rotation angle detecting means 96 detects an appropriate rotation angle in accordance with the image signal representing the composed image and feeds a signal to the image recording section 30 or the image recording section 80. Also, reconstruction means 98 of the image processing section 92 receives the image signal from the secondary storing means 90b. The reconstruction means 98 performs image processing on the image signal and reconstructs a three-dimensional image.

In the radiation image recording apparatus 1 of FIG. 1A, two radiation blocking plates 8 and 14 are utilized. Alternatively, the radiation blocking plate 14 close to the radiation source 10 may be omitted, and the radiation source 10 may have the functions of the radiation blocking plate 14. Specifically, the radiation source 10 itself may have the functions for producing the fan beam-like radiation. In such cases, the radiation image recording apparatus in accordance with the present invention may be constituted as a radiation image recording apparatus provided with a radiation detector for receiving radiation, which carries image information of an object, and feeding out an image signal representing the image information of the object, the apparatus comprising:

i) radiation irradiating means for irradiating radiation, which has been restricted to a predetermined irradiation range, to the object and being capable of altering the direction of irradiation of the radiation, ii) a radiation blocking plate, which is located between the object and the radiation detector and which has a slit aligned with primary passing radiation having passed through the object, iii) slit control means for shifting stepwise the direction of irradiation of the radiation, whose direction has been adjusted by the radiation irradiating means and the radiation blocking plate in co-operation with each other, and iv) rotation control means for rotating the radiation irradiating means, the radiation blocking plate, and the radiation detector around the object.

Also, in the embodiments described above, each of the radiation blocking plates has the flat surface-like shape. However, in the radiation image recording apparatus in accordance with the present invention, the radiation blocking plates need not necessarily have the flat surface-like shape. For example, each of the two radiation blocking plates may have a spherical shape with a concave surface facing the radiation source, such that the two spherical radiation blocking plates have the center of curvature at an identical point. The two spherical radiation blocking plates may be shifted stepwise around the center of curvature.

What is claimed is:

1. A radiation image recording method, comprising the steps of:

i) locating a radiation source and a radiation detector with an object intervening therebetween, ii) locating a set of radiation blocking plates, each of which has at least one slit, between the radiation source and the radiation detector such that the object intervenes between the radiation blocking plates, and such that the slits of the radiation blocking plates are aligned in a straight line with the radiation source, iii) shifting the set of the radiation blocking plates stepwise in a direction along which radiation having been produced by the radiation source scans the object, such that the state in which the slits of the radiation blocking plates and the radiation source are aligned with one another in the straight line is kept, iv) after each step of the shifting, rotating the radiation source, the set of the radiation blocking plates, and the radiation detector around the object, and v) recording radiation image patterns of the object during the rotation.

2. The method of claim 1, wherein slits of the radiation blocking plates and the radiation source are aligned by shifting of the slits within the blocking plates.

3. A radiation image recording apparatus, comprising:

i) a radiation source, ii) a radiation detector, which is located so as to stand facing the radiation source with an object intervening between the radiation detector and the radiation source, iii) a set of radiation blocking plates, each of which has at least one slit and which are located between the radiation source and the radiation detector such that the object intervenes between the radiation blocking plates, and such that the slits of the radiation blocking plates are aligned in a straight line with the radiation source, iv) means for shifting the set of the radiation blocking plates stepwise in a direction along which radiation having been produced by the radiation source and having been shaped by the slit of the radiation blocking plate close to the radiation source into a fan beam scans the object, such that the state in which the slits of the radiation blocking plates and the radiation source are aligned with one another in the straight line is kept, v) means for rotating the radiation source, the set of the radiation blocking plates, and the radiation detector around the object after each step of the shifting, and vi) image recording means for recording radiation image patterns of the object at a plurality of positions of rotation during the rotation.

4. The apparatus of claim 3, wherein the means for shifting keeps alignment of the slits of the radiation blocking plates and the radiation source by shifting of slits within the blocking plates.

* * * * *